(12) United States Patent
Polukhtin et al.

(10) Patent No.: US 8,933,261 B2
(45) Date of Patent: Jan. 13, 2015

(54) BENZOPHENONE-BASED CHROMOPHORIC CROSSLINKERS AND REAGENTS FOR INCORPORATION OF BIOTIN OR OTHER HAPTENS INTO MACROMOLECULES

(71) Applicant: Andrei Polukhtin, Scottsdale, AZ (US)

(72) Inventors: Andrei Polukhtin, Scottsdale, AZ (US); Willy Chang, Scottsdale, AZ (US); Leopoldo G. Mendoza, Scottsdale, AZ (US)

(73) Assignee: Andrei Polukhtin, Scottsdale, AZ (US)

( * ) Notice: Subject to any disclaimer, the term of this patent is extended or adjusted under 35 U.S.C. 154(b) by 0 days.

(21) Appl. No.: 13/804,602

(22) Filed: Mar. 14, 2013

(65) Prior Publication Data

US 2014/0275482 A1        Sep. 18, 2014

(51) Int. Cl.
*C07C 69/76*        (2006.01)
*C07D 495/04*      (2006.01)
*C07D 207/46*      (2006.01)
*C07D 225/08*      (2006.01)

(52) U.S. Cl.
CPC ............ *C07D 495/04* (2013.01); *C07D 207/46* (2013.01); *C07D 225/08* (2013.01)
USPC ............................................................ 560/8

(58) Field of Classification Search
None
See application file for complete search history.

(56) References Cited

U.S. PATENT DOCUMENTS 4,727,140 A * 2/1988 Meisel et al. .................. 544/92

OTHER PUBLICATIONS

Arbi et al. Journal of Organometallic Chemistry 696 (2011) 1038-1048.*
Yokoshima et al. Bioorganic & Medicinal Chemistry Letters 19 (2009) 6869-6871.*
Kan et al. Org. let, 2007, 9, 2055-2058.*

* cited by examiner

*Primary Examiner* — Brandon Fetterolf
*Assistant Examiner* — Ana Z Muresan
(74) *Attorney, Agent, or Firm* — Birch, Stewart, Kolasch & Birch, LLP

(57) ABSTRACT

Compounds for UV-Vis detectable incorporation of a crosslinker a hapten into a protein or macromolecules are disclosed. The compounds comprise bis heterofunctional crosslinkers or haptens containing a chromophoric group that is incorporated into the linker that is positioned between a reactive linking moiety and a biotin molecule. The incorporation of the crosslinker or hapten into a protein or other macromolecules may be detected by UV-Vis spectroscopy.

11 Claims, 1 Drawing Sheet

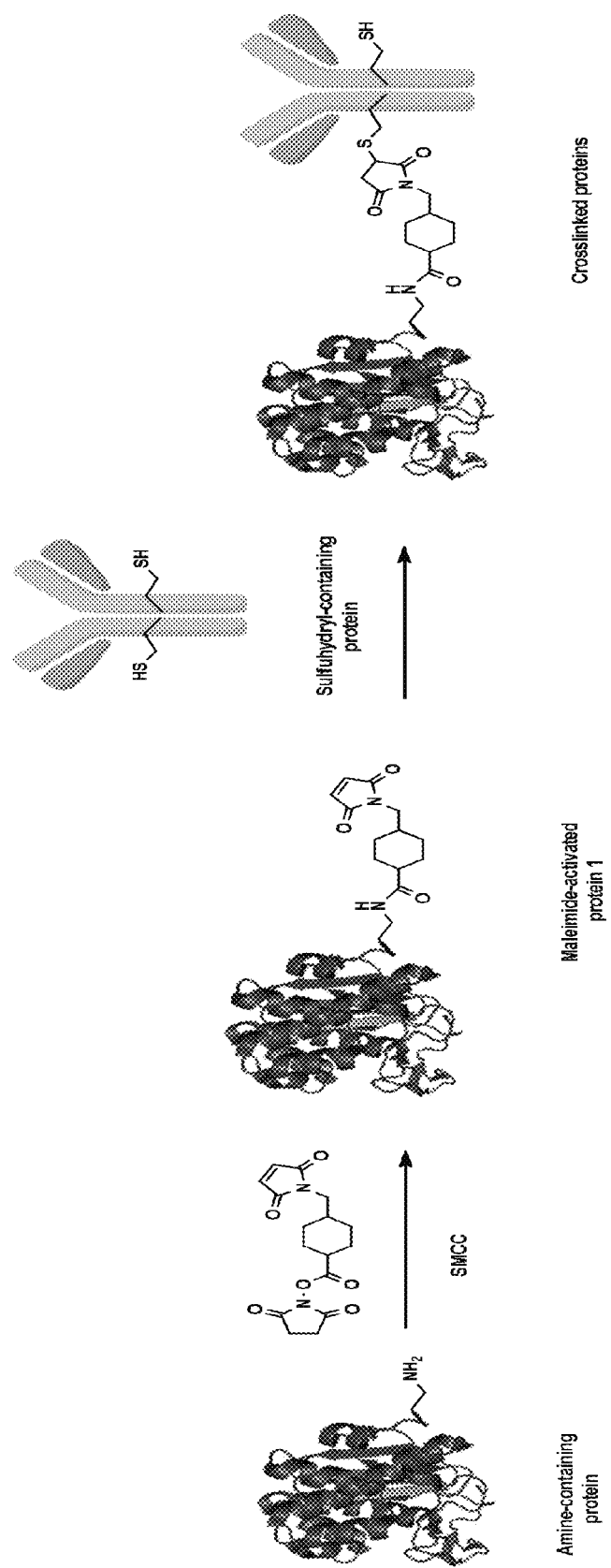

BENZOPHENONE-BASED CHROMOPHORIC CROSSLINKERS AND REAGENTS FOR INCORPORATION OF BIOTIN OR OTHER HAPTENS INTO MACROMOLECULES

FIELD OF THE INVENTION

The present invention relates to compounds used to label or crosslink biomolecules for research, diagnostic and therapeutic purposes. In particular, the invention relates to chromophoric compounds that may crosslink or be conjugated to biomolecules, such as proteins and nucleic acids. Such compounds may be incorporated into linkers that may be used to link a ligand to a biomolecular probe allowing quantitation of the ligand bound to that molecular probe.

BACKGROUND OF THE INVENTION

Crosslinking is the process of joining two or more molecules by a covalent bond. Crosslinking reagents contain reactive ends to specific functional groups (primary amines, sulfhydryls, etc.) on proteins or other molecules. Because of the availability of several chemical groups in proteins and peptides that may be targets for reactions, proteins and peptides are readily conjugated and otherwise studied using crosslinking methods.

The traditional way to couple two proteins, for example through an amine (—NH2) functional group on one protein and a sulfhydryl (—SH) group on the other, is by using a heterobifunctional crosslinker that contains a N-hydroxysuccinimide (NHS) ester and a maleimide group, e.g. SMCC. NHS esters react with primary amines at pH 7-9 to form covalent amide bonds. Maleimides react with sulfhydryl groups at pH 6.5-7.5 to form stable thioether bonds. The traditional (above mentioned) heterobifunctional crosslinking strategy using SMCC is outlined in FIG. 1.

Although these reagents have been used successfully to obtain numerous protein-protein conjugates, they possess a major inherent deficiency; it is impossible to determine the amount of incorporation of crosslinkers, e.g. degree of activation of a protein with SMCC. In addition, some reactive groups, e.g. maleimide or NHS can undergo rapid hydrolysis, which makes precise determination of the incorporation of a crosslinker into the activated intermediate impossible.

Therefore, there is a need in the field for bis-heterofunctional crosslinking reagents that allow for very quick, non-destructive determination of crosslinker incorporation into an activated peptide biopolymer. The extensive use of avidin/biotin technology in immunology and diagnostic medicine is based on numerous factors. The high binding affinity between avidin and biotin yields an avidin-biotin complex having very high stability. Avidin is a tetrameric glycoprotein made up of four identical subunits. Therefore, four biotin molecules are capable of binding to one avidin molecule, Adv. Prot. Chem. 29:85 (Green, N. M., 1975), thereby increasing the sensitivity of constructed probe systems, and allowing the crosslinking of two or more biotin-labeled materials.

The disassociation constant for the avidin-biotin complex is $10^{-15}$ at neutral pH, Biochem. J., 89:585 (Green, N. M., 1963). This interaction is one of the strongest non-covalent associations found in nature. Biotin is deeply bound in a groove in the avidin molecule with the carboxyl group about 9 angstroms below the protein surface, Biochem. J., 125:781 (Green, N. M., et al., 1971). The widespread use of biotin-avidin technology is based upon the fact that a biotin molecule is easily coupled via a covalent linkage to a protein, while maintaining substantially all the biological properties of the protein and the binding capacity of biotin to avidin.

The extremely high binding constant and fast kinetics of binding and the stability of avidin under a variety of conditions make this an ideal ligand/receptor pair for these purposes. Biotin has been modified to include amino, thiol and carbohydrate reactive moieties, i.e. succinimidyl ester, maleimido and hydrazide respectively, to allow easy incorporation into a large variety of biomolecules. To accomplish detection of an analyte, biotin is conjugated to a probing biomolecule, such as an antibody or an oligonucleotide. Following binding of the biotinylated biomolecule to its receptor or complement, an avidin/reporter conjugate, such as an avidin/fluorophore conjugate or a avidin/reporter enzyme conjugate is added and allowed to bind to a biotinylated probe and visualized by fluorescence detection or addition of a substrate that emits light or precipitates a colored insoluble product on enzymatic processing (Heitzmann H., Richards F. M., Proc. Natl. Acad. Sci. USA 71:3537-3541, 1974; Diamandis E. P., Christopoulos T. K., Clin. Chem. 37:625-636, 1991; Wilchek M. Methods Enzymol Vol. 184, 1990; Savage, M. D. et al., 1992 Avidin-Biotin Chemistry: A Handbook. Rockford, Ill.: Pierce Chemical Co.).

Following conjugation, it is important to confirm that the probe molecule has been biotinylated and to quantify the number of biotins conjugated to the probe molecule. To this end two multi-step indirect assays have been developed. The first assay is the HABA ([2-(4'-hydroxyazobenzene)]benzoic acid) assay developed by Green (Green, N. M. Biochem. J., 94, 23c-24, 1965). To quantify biotin label incorporation, a solution containing the biotinylated protein is added to a mixture of HABA and avidin. Because of its higher affinity for avidin, biotin displaces the HABA from its interaction with avidin and the absorption at 500 nm decreases proportionately. By this method, an unknown amount of biotin present in a solution can be evaluated in a single cuvette by measuring the absorbance of the HABA-avidin solution before and after addition of the biotin-containing sample. The change in absorbance relates to the amount of biotin in the sample.

The second more sensitive fluorescence-based multi-step assay developed by Molecular Probes is the 'Fluoreporter Biotin Quantitation Assay' that is based on fluorescence resonance energy transfer (FRET) quenching wherein an avidin molecule is labeled with a fluorophore and its binding sites are occupied with a fluorescent molecule that quenches the covalently linked fluorophore until the quencher in the binding site is displaced by a higher binding biotin molecule resulting in fluorescence of the covalently attached fluorophore. While this assay is sensitive to 50-100 .rho.mol range it requires many processing steps and a fluorimeter or multi-well fluorimeter. It is also recommended that the biotinylated protein be digested prior to the assay to expose any sterically encumbered biotins.

The direct method of hapten incorporation developed by Solulink Inc (US Pat Pub 20080221343) is based on incorporation of hydrazone-based, spectrophotometrically quantifiable group into a linker. The incorporation of the hapten into a protein or other macromolecule can be detected by non-destructive UV-Vis spectroscopy. While the incorporation of the hydrazone moiety into a linker allows for direct, and non-destructive determination of degree of incorporation, it possess a major disadvantage with regard to the long term stability of the hydrozone moiety. Under certain conditions the hydrozone bond can undergo hydrolysis resulting in dissociation of hapten from analyte Angew. Chem. Int. Ed, 49:11 (Anouk, D., et al., 2010).

Consequently there is a need in the field for a assay wherein the number of biotins covalently linked to a biomolecule con be determined by direct methods, such as spectroscopic means, without compromising of long-time stability of conjugates.

BRIEF SUMMARY OF THE INVENTION

Although methods exist for detecting specifically binding complexes in solution by the action of a diagnostic reagent, no method exists for accurately and non-destructively confirming whether the crosslinking reagent has been linked to a biomolecule.

Therefore, it is an object of the present invention to provide technology for accurately and non-destructively detecting the presence of a crosslinker or hapten linked to a biomolecule, such as a protein or polynucleotide.

It is a further object of the present invention to provide technology for accurately and non-destructively determining the amount of crosslinker or hapten incorporated into molecules, such as proteins or polynucleotides.

The present invention encompasses compounds comprising crosslinkers or haptens, such as biotin bound directly or indirectly to a chromophoric group, and a reactive group, wherein the incorporation of the hapten in a protein or macromolecule can be confirmed directly by detecting the chromophoric group.

The present invention provides benzophenone-based, spectrophotometrically quantifiable crosslinkers and hapten labeling reagents of the formula

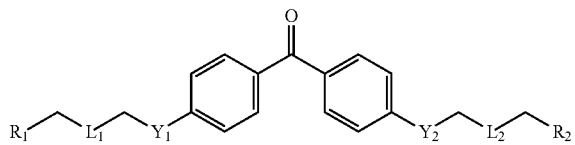

wherein: $R_1$ and $R_2$ are independently a reactive group
$Y_1$ and $Y_2$ are independently $N-R_4$ or $O$
$R_4$ is selected from H, lower alkyl ($C_1$-$C_{10}$) or PEG
$L_1$ and/or $L_2$ is a linker Exemplary Reactive Groups

| Reactive Group | Target Functional Group |
|---|---|
| Carbodiimide | Amine/Carboxyl |
| Carbonyl | Hydrazide |
| Diazirine | Nonselective |
| Hydrazide | Carbohydrate (oxidized) |
| Hydroxymethyl Phosphine | Amine |
| Imidoester | Amine |
| NHS-ester | Sulfhydryl |
| PFP-ester | Amine |
| Psoralen | Amine |
| Pyridyl Disulfide | Sulfhydryl |
| Vinyl Sulfone | Sulfhydryl, amine, hydroxyl |
| Terminal Alkyne | Azide |
| Azide | Terminal alkyne, cyclooctyne |
| Trans-Cyclooctene | Tetrazine |

In another aspect of the present invention encompasses compounds comprising of formula:

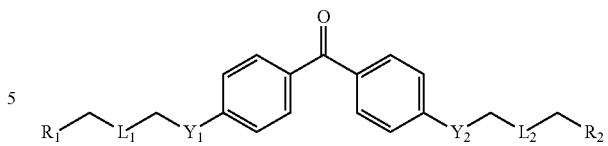

wherein: $R_1$ is a reactive group
$R_2$ is a hapten
$Y_1$ and $Y_2$ are independently $N-R_4$ or $O$
$R_1$ is selected from H, lower alkyl ($C_1$-$C_{10}$) or PEG
$L_1$ and/or $L_2$ is a linker

BRIEF DESCRIPTION OF THE DRAWINGS

FIG. 1: A schematic representation of the chemistry for the crosslinking of two proteins using SMCC;

DETAILED DESCRIPTION OF THE INVENTION

Unless defined otherwise, all terms used herein have the same meaning as is commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "biomolecule" as used herein refers to a compound of biological origin, or of biological activity. Biomolecules include for example a nucleic acid, a nucleotide, a protein, an amino acid, a carbohydrate monomer and a polysaccharide. If the biomolecule is a nucleic acid it may be DNA, cDNA, RNA, or PNA and may comprise natural or unnatural bases or internucleotide linkages, such as phosphodiesters, phosphorothioates, phosphoramidites or peptide nucleic acids.

The term "chromophore" as used herein refers to a compound that absorbs certain wavelengths of ultraviolet or visible light (UV-Vis)

The term "reactive group" as used herein refers to molecules used for binding one molecule to another based on the presence of a particular chemical group on the molecule of interest. Some commercially sold molecules referred to herein as linking moieties include those that react with free amines on the target molecule, such as N-hydroxysuccinimidyl, p-nitrophenyl, pentafluorophenyl and N-hydroxybenzotriazolyl ester, and those that react with free sulfhydryls present on the target molecule such as maleimido, alpha-haloacetamido and pyridyldisulfides.

The term "linker" is a covalent linkage having 1-48 non-hydrogen atoms selected from the group consisting of C, N, O, P, and S and composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds;

The term "ligand/receptor couple" as used herein refers to a pair of molecules having a substantially high affinity for binding specifically to one another. One example of such a binding pair would be a receptor on a cell and the ligand that binds that receptor. Another example would be biotin and avidin, which are two molecules that have a strong affinity for binding each other and having an association constant of around $10^{15}$. Other pairs include Peptide S and ribonuclease A, digoxigenin and its receptor and complementary oligonucleotide pairs.

Various methods exist which may be employed to bind the extended linking group to a macromolecule or fragment. For example, to facilitate this binding the extended linking group may be attached to biomolecule-reactive groups, such as active ester groups, amino groups, sulfhydryl groups, carbohydrate groups, azido groups or carboxy groups. A variety of methodologies exist for reacting biomolecule-reactive groups with macromolecules or macromolecule fragments. Examples of such methodologies are photo-crosslinking and glutaraldehyde crosslinking. Still other methods for effecting such coupling will occur to those skilled in the art. See, for examples of such methods: Hermanson, G. T., Bioconjugate Techniques, Elsevier Science, London, 2008.

Active ester groups of the present invention should be selected such that they will not impair linkage of the extended linking group to a protein or macromolecule. Those skilled in the art will appreciate that active esters such as, for example, N-hydroxysuccinimide or N-hydroxysulfosuccinimide may be employed in the present invention. Alternatively, primary amino groups on the extended linking group may be coupled to primary amino groups on a protein by glutaraldehyde. Amino groups on proteins may be coupled to carboxy groups on the extended linking group. In addition, the extended linking group may be modified with a nitrophenyl azide such that coupling to a protein will occur when irradiated with visible light. Still other methods for effecting such coupling will occur to those skilled in the art.

Chromophoric groups suitable for use in the present invention may be selected from various substituted benzophenones. These chromophoric groups absorb energy in the electromagnetic spectrum, usually in the ultraviolet region.

Chromophoric groups must be chosen such that they will not interfere with the binding of the hapten to the anti-hapten and so that they will absorb energy at a different wavelength than the biomolecule to be labeled. Therefore, chromophoric groups that do not interfere in the hapten/anti-hapten interaction and that absorb at wavelengths greater than 300 nm are preferred for labeling proteins, polynucleotides, and fragments thereof. The more preferred chromophore absorb at wavelengths greater than 300 nm. Determination of these chromophoric groups may be conveniently made by measuring chromophore absorbance.

One embodiment of the invention is a method of synthesis of substituted-benzophenone chromophoric groups suitable for incorporation into crosslinkers and hapten-modification reagents. Many substituted benzophenones are commercially available, but none of them can be used for incorporation into crosslinkers and hapten-modification reagents.

The preferred method of making bis-p-substituted benzophenones is the reaction of p-substituted aryl-acetyl chloride with activated, p-substituted aromatic compounds in the presence of catalyst according to equation 1. The preferred catalyst is aluminum chloride, and the preferred solvent is dichloromethane. However, other catalysts known in the art can be used, including, but not limited aluminum bromide or phosphoric acid.

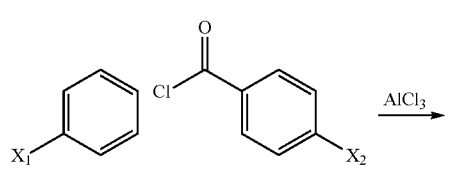

Eq 1

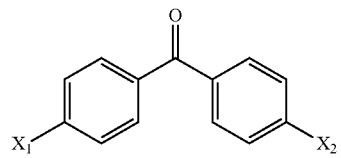

To one skilled in the art there are multiple variations that can affect the optimal range of conditions under which the core of chromophoric linker can be prepared. In addition to the inherent differences between performing this reaction at bench scale versus large commercial processes, there are other variables including: (a) the concentration of reagents and catalyst; (b) the reactivity of reagents; (c) temperature at which the reaction is run; (d) the rate of addition of reactants An important aspect of this invention is to provide valuable spectrophotometrically quantifiable compounds, which are precursors to other compounds that can be used in variety of biological applications. To be valuable in a particular application, $X_1$ and $X_2$ undergo functional group manipulations to achieve the functionality, which is desirable for the particular application of UV-Vis active crosslinking reagent or hapten labeling reagent.

Table 1 summarizes some of the preferred combination of X1 and X2. These examples are not meant to be limiting, but rather representative of some more useful functionality used in many biological applications.

TABLE 1

| $X_1/R_1$ | $X_2/R_2$ |
|---|---|
| NHS-ester | NHS-ester |
| NHS-ester | Maleimide |
| NHS-ester | Vinyl Sulfone |
| NHS-ester | Pyridyl Disulfide |
| NHS-ester | Azide |
| NHS-ester | Terminal alkyne |
| NHS-ester | Cyclooctyne |
| NHS-ester | Trans-Cyclooctene |
| NHS-ester | Tetrazine |
| NHS-ester | Biotin |
| Maleimide | Azide |
| Maleimide | Terminal alkyne |
| Maleimide | Cyclooctyne |
| Maleimide | Trans-Cyclooctene |
| Maleimide | Tetrazine |
| Maleimide | Biotin |

In other aspect, the present invention relates to spectrophotometrically quantifiable crosslinkers. Crosslinking is the process of joining two or more molecules by a covalent bond. Crosslinking reagents contain reactive ends to specific functional groups (primary amines, sulfhydryls, etc.) on proteins or other molecules. Because of the availability of several chemical groups in proteins and peptides that may be targets for reactions, proteins and peptides are readily conjugated and otherwise studied using crosslinking methods. The exemplary spectrophotometrically quantifiable heterobifunctional crosslinking reagent of the invention has formula I

I

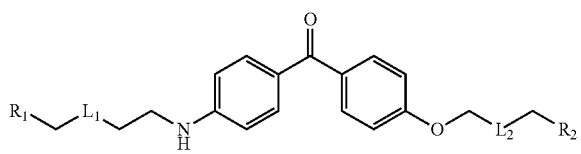

wherein $R_1$ and $R_2$ are independently selected from reactive groups capable of modifying biomolecules. Examples of such reactive groups are outlined in table 1. The preferred embodiment of this disclosure, the heterobifunctional crosslinking reagent has Formula II

II

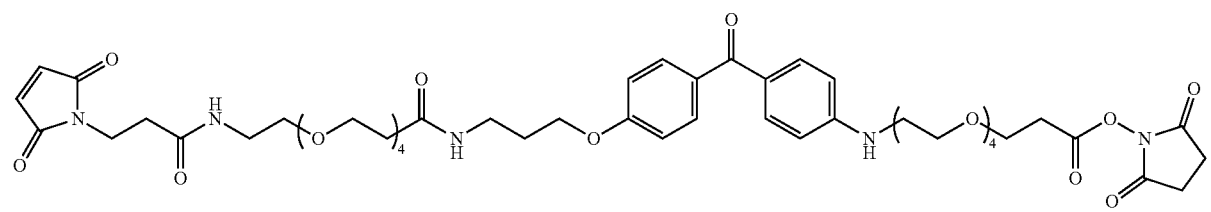

To one skilled in the art it will be apparent that there are multiple variations of thiol-reactive, amine-reactive, as well as linkers, connecting biomolecule-reactive groups with the core of chromophoric group.

In still other aspect, the present invention relates to bio-orthogonal chemistry. The term bioorthogonal chemistry refers to any chemical reaction that can occur in the presence of rich functionalities of living systems/biological media without interfering with native biochemical processes. In this strategy, one component of the conjugate is modified with a bioorthogonal functional group, while in a separate reaction, the other component is activated with a complementary functional group of the bioorthogonal ligation pair. The two bioorthogonally-activated components are then mixed together and spontaneously react to form the specific conjugate. In certain embodiments, the bio-orthogonal reaction is a Cu-catalyzed version of Huisgen 1,3-dipolar cycloaddition between an azide and terminal alkyne. In other embodiments, the reaction is carried out in the absence of such a catalyst.

Exemplary 1,3-dipole-functional compounds include, but are not limited to, azides, nitrile oxides, nitrones, and diazo compounds. The exemplary spectrophotometrically quantifiable heterobifunctional crosslinking reagent has formula III

III wherein $R_1$ is selected from reactive groups capable of modifying biomolecules, $R_3$ is either a terminal alkyne or a 1,3-dipole-functional group selected from azides, nitrile oxides, nitrones, and diazo groups, $L_1$ and $L_2$ are independently linkers. Examples of reactive groups capable of modifying biomolecules are outlined in table 1. With a preferred embodiment of the invention, the spectrophotometrically quantifiable 1,3-dipole-functional compound and terminal alkyne has Formula IV or V.

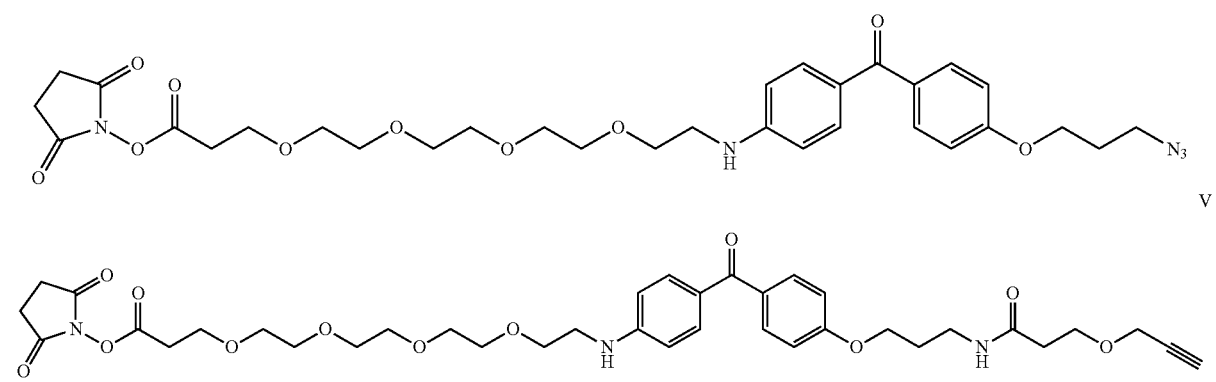

In another aspect, the present invention relates to trans-cyclooctenes and tetrazines. The inverse-electron demand Diels-Alder cycloaddition reaction of trans-cyclooctenes (TCO) with tetrazines is a bioorthogonal reaction that possesses exceptional kinetics ($k>800$ $M^{-1}$ $s^{-1}$) and selectivity. Such excellent reaction rate constants are unparalleled by any other bioorthogonal reaction pair described to date. Exemplary dienophile compounds include, but are not limited to, norbornene, and trans-cyclooctenes. Exemplary spectrophotometrically quantifiable dienophile reagents have formula VI

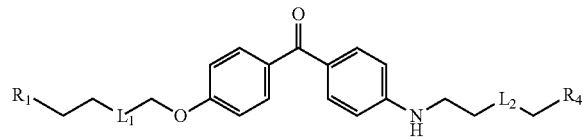

VI wherein $R_1$ is selected from reactive groups capable of modifying biomolecules, $R_4$ is a dienophile group selected from norbornene, or trans-cyclooctene, and $L_1$ and $L_2$ are independently linkers. Examples of reactive groups capable of modifying biomolecules are outlined in table 1. With a preferred embodiment of the invention, the spectrophotometrically quantifiable 1,3-dipole-functional compounds and terminal alkyne has Formula IV or V. Preferable dienophile compounds are trans-cyclooctenes. The preferred spectrophotometrically quantifiable inverse-electron demand Diels-Alder cycloaddition reaction reagent has formula VII or VIII embodiment of this invention provides hapten labeling reagents with incorporated spectrophotometrically quantifiable benzophenone moieties. An exemplary spectrophotometrically quantifiable heterobifunctional crosslinking reagent has formula IX

IX wherein $R_1$ is selected from reactive groups capable of modifying biomolecules, $R_3$ is a hapten selected from, but not limited to, biotin, desthiobiotin, and digoxigenin, and $L_1$ and $L_2$ are independently linkers. Examples of reactive groups capable of modifying biomolecules are outlined in table 1. The preferred spectrophotometrically quantifiable, amino-,

VII

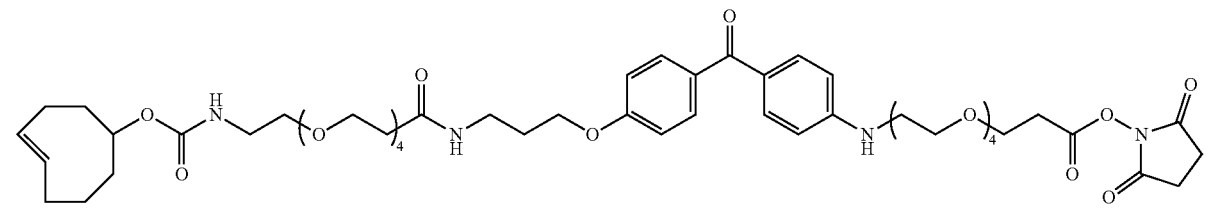

VIII

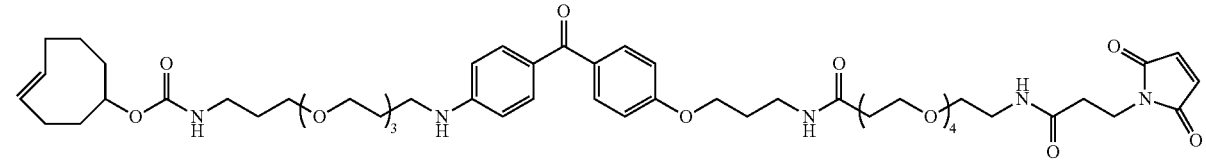

In still other aspect, the present invention relates to spectrophotometrically quantifiable hapten labeling reagents. Exemplary haptens include, but are not limited to, biotin, desthiobiotin, and digoxigenin. The common problems associated with standard biotinylation procedures is the inability to directly determine if labeling worked properly or to what degree. Often this can result in the reduction or loss of protein activity due to over-biotinylation. In addition, protein activity might vary from labeling experiment to labeling experiment due to a different degree of biotin incorporation. A further and thiol-reactive biotin labeling reagent has formula X or XI. An amino-, and thiol-reactive biotin biotin labeling reagent contains a chromophoric benzophenone moiety for spectrophotometric quantitation and two PEG linkers that are required to retain the binding affinity of biotin to streptavidin. This tri-functional molecule can be readily quantified spectrophotometrically following conjugation to a biomolecule because of its unique molar extinction coefficient (ca. 20000) and its unique absorbance at 350 nm.

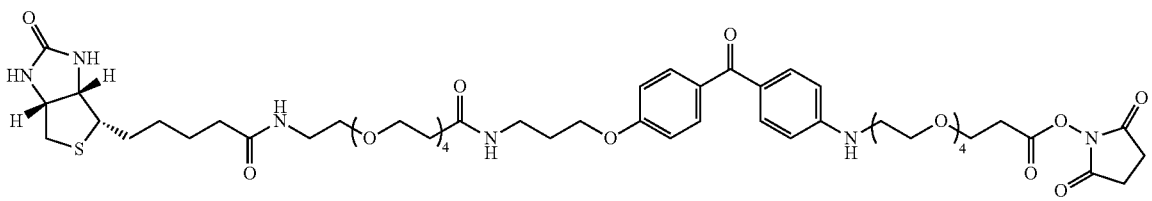

X

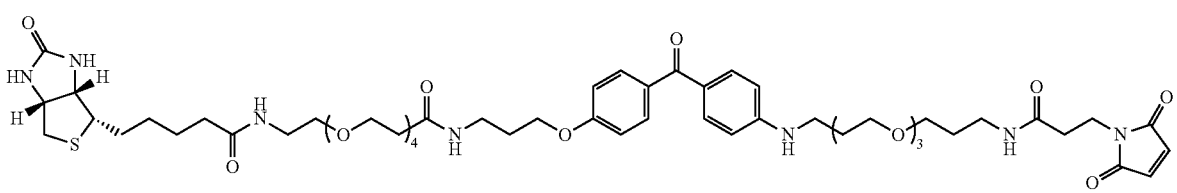

XI

To one skilled in the art there are multiple variations of reactive groups capable of modifying biomolecules, haptens, and linkers for connecting biomolecule-reactive groups with the core of chromophoric group.

In yet another aspect, the invention provides a method of labeling biomolecules with compounds of this invention. It is preferred that protein or antibody labeling is carried out in a buffer optionally including an organic co-solvent, under basic pH conditions, and at room temperature. It is also preferred that the labeled antibody be purified by dialysis or by gel permeation chromatography to remove any unconjugated compounds. Those of skill in the art will know ways and means of purification.

In one aspect, biomolecules can be labeled according to the present invention by means of a kit. In certain instances, the kit comprises a buffer, a compound as disclosed in the instant application, purification media, and the manual. Preferably, the kit contains a coupling buffer such as 1 M $KH_2PO_4$ (pH 5), optionally with added acid or base to modify the pH (e.g., pH 7.5 is preferred for reactions with succinimide esters, and pH 6.5 is preferred for reactions with maleimides). Preferably, the buffer does not absorb the light in the same region where chromophoric group has absorbance band.

While the invention has been described with references to a preferred embodiments, those skilled in the art will understand various changes may be made and equivalents may be substituted for elements thereof without departing from the scope of the invention. In addition, many modifications may be made to adapt a particular situation or materials to the teaching of the invention without departing from the essential scope thereof. Therefore, it is intended that the invention not to be limited to the particular embodiments disclosed, but that the invention will include all embodiments falling within the scope of the appended claims. In this application all units are the metric system, and all amounts and percentage are by weight, unless otherwise expressly indicated. Also, all citations referred herein are expressly incorporated herein by references.

Experimental Embodiments

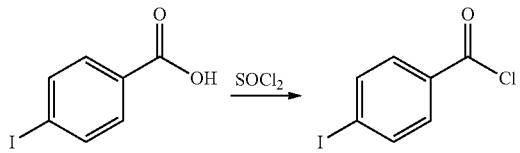

Thionyl chloride (36.0 g, 302 mmol) was added to a suspension of 4-iodobenzoic acid (50.0 g, 202 mmol) in anhydrous DCM (300 ml) followed by a few drops of DMF and the reaction mixture was stirred overnight at r.t. Upon completion, reaction flask was concentrated under reduced pressure to yield 51.6 g (96.0% yield) of crude 4-iodobenzoyl chloride that was used in the next step without further purification.

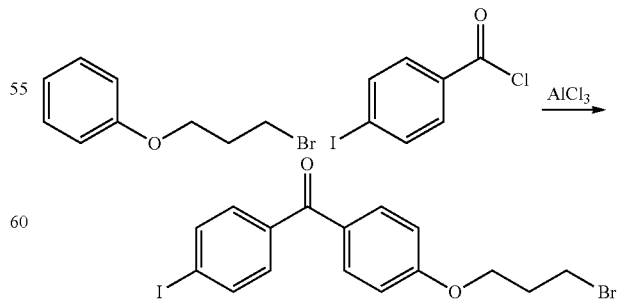

A solution of (3-bromopropoxy)benzene (44.4 g, 206 mmol) in DCM was added dropwise to a suspension of aluminum trichloride (27.5 g 206 mmol) and 4-iodobenzoyl chloride (50.0 g, 188 mmol) in anhydrous DCM (330 ml) at −78° C. ca. Reaction turned yellow and was allowed to warm to r.t. and stir for 4 hs. Upon completion, reaction was brought to 0° C., diluted with DCM, and quenched with 5% HCl. The organic layer was separated, washed additionally with brine, and dried over anhydrous Na₂SO₄. The organic layer was concentrated under reduced pressure and re-crystallized using EtOAc to afford 60.1 g (71.8% yield) of (4-(3-bromopropoxy)phenyl)(4-iodophenyl)methanone as grey solid.

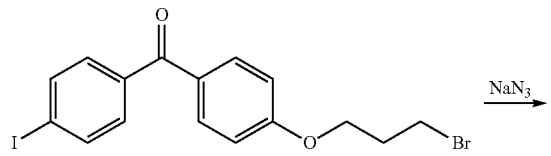

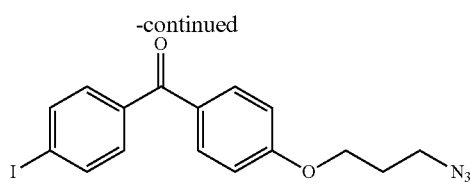

A solution of (4-(3-bromopropoxy)phenyl)(4-Iodophenyl)methanone (50.0 g, 112 mmol), and sodium azide (10.2 g, 157 mmol) was dissolved in DMF (300 ml). The reaction was heated to 45° C. and left to stir overnight. Upon completion, the reaction mixture was filtered to remove sodium salt and concentrated under reduced pressure. The crude was then further extracted with chloroform, the organic layer was washed with brine, and dried over anhydrous sodium sulfate to afford 40.3 g (88.0% yield) of (4-(3-azidopropoxy)phenyl)(4-iodophenyl)methanone as grey solid.

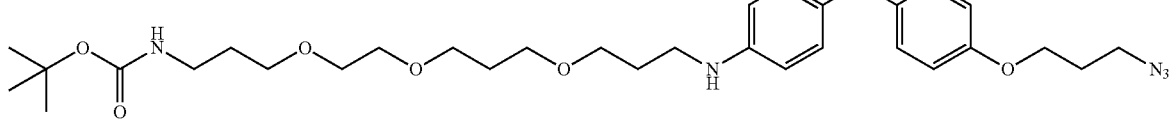

2-Acetylcyclohexanone (826 mg, 5.89 mmol), cesium carbonate (12.8 g, 39.3 mmol), tert-butyl (3-(2-(3-(3-aminopropoxy)propoxy)ethoxy)propyl)carbamate (6.32 g, 20.63 mmol), and copper(I) iodide (561 mg, 2.95 mmol) was added to a solution of (4-(3-azidopropoxy)phenyl)(4-iodophenyl)methanone (8.0 g, 19.7 mmol) in anhydrous DMF (55 ml). The flask was vacuumed and backfilled with argon three times, sealed and stirred r.t. for 3-4 hs. Upon completion, reaction was concentrated and purified with silica gel chromatography (EtOAc:Hex gradient) to yield 10.5 g (91.0% yield) of tert-butyl (3-(2-(2-(3-((4-(4-(3-aminopropoxy)benzoyl)-phenyl)amino)propoxy)ethoxy)ethoxy)propyl)carbamate as yellow oil.

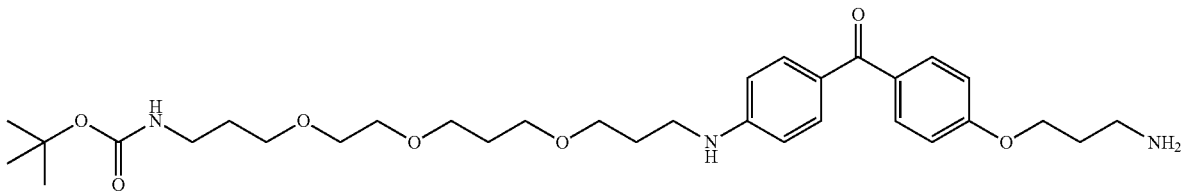 [SMILES: CC(C)(C)OC(=O)NCCCOCCOCCCOCCCNc1ccc(C(=O)c2ccc(OCCCN)cc2)cc1]

Triphenylphosphine (1.64 g, 6.25 mmol) was added to a solution of tert-butyl-(3-(2-(2-(3-((4-(4-(3-aminopropoxy)benzoyl)-phenyl)amino)propoxy)ethoxy)ethoxy)propyl)carbamate in Ether:THF (1:1, 20 mL) at 0° C. followed by the addition of water (225 mg, 12.5 mmol). The reaction was stirred at r.t. overnight. Upon completion, the reaction was concentrated and purified by silica gel chromatography (EtOAc to EtOAc:MeOH gradient with 1% TEA) to provide 1.91 g (80.0% yield) of tert-butyl (3-(2-(3-(3-((4-(4-(3-aminopropoxy)benzoyl)phenyl)amino)propoxy)propoxy)ethoxy)propyl)carbamate as yellow oil.

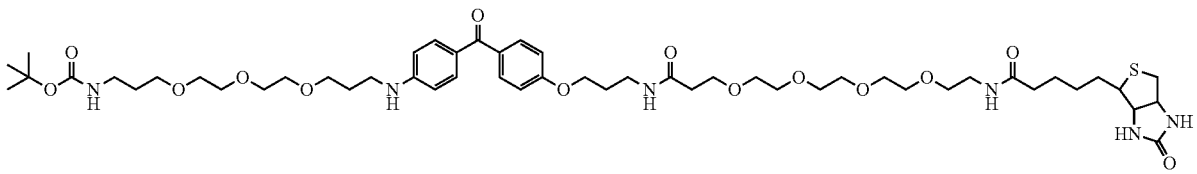 [SMILES: CC(C)(C)OC(=O)NCCCOCCOCCOCCCNc1ccc(C(=O)c2ccc(OCCCNC(=O)CCOCCOCCOCCOCCNC(=O)CCCCC3SCC4NC(=O)NC43)cc2)cc1]

NHS-dPEG4-biotin (Quanta BioDesign Ltd, 9.21 g, 17.9 mmol) was added to a solution of tert-butyl (3-(2-(3-(3-((4-(4-(3-aminopropoxy)benzoyl)phenyl)amino)propoxy)propoxy)ethoxy)propyl)carbamate (9.31 g, 17.1 mmol) in anhydrous DCM (60 ml) and the reaction mixture was stirred at r.t. for 3 hs. Upon completion, reaction was concentrated under reduced pressure and purified by silica gel chromatography (DCM to DCM:MeOH, gradient) to yield 16.1 g (94.0% yield) of tert-butyl (3-(2-(2-(3-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)propoxy)ethoxy)ethoxy)propyl)carbamate as slightly yellow oil.

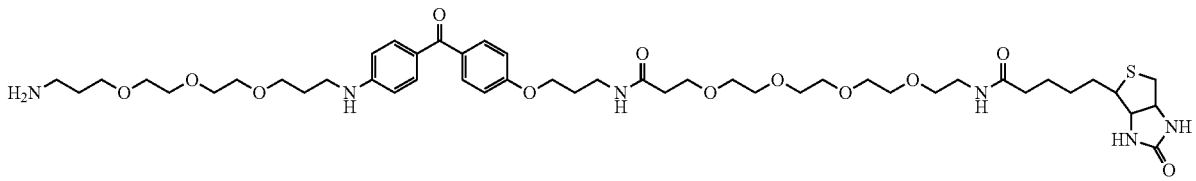 [SMILES: NCCCOCCOCCOCCCNc1ccc(C(=O)c2ccc(OCCCNC(=O)CCOCCOCCOCCOCCNC(=O)CCCCC3SCC4NC(=O)NC43)cc2)cc1]

tert-butyl (3-(2-(2-(3-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)propoxy)ethoxy)ethoxy)propyl)carbamate (16.1 g, 15.92 mmol) was dissolved in a solution of DCM:TFA (2:1, 96 ml) and the reaction mixture was stirred for ca. 1 h at r.t. Upon completion, reaction was then concentrated under reduced pressure, co-evaporated with toluene, and dried on pump for 5 hs to yield 14.13 g (98% yield) of crude N-(3-(4-(4-((3-(2-(2-(3-aminopropoxy)ethoxy)ethoxy)propyl)amino)benzoyl)phenoxy)propyl)-1-(5-(2-oxohexahydro-1H-thieno[3,4-d]imidazol-4-yl)pentanamido)-3,6,9,12-tetraoxapentadecan-15-amide as yellow oil.

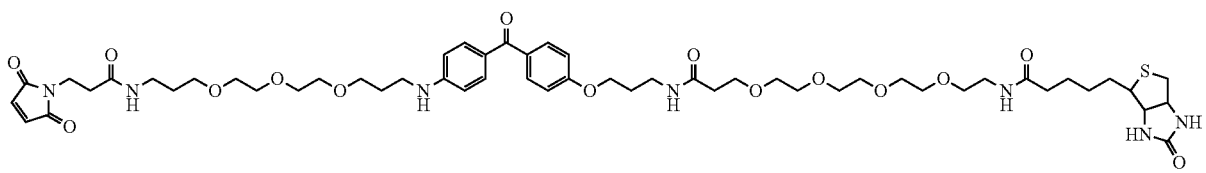 [SMILES: O=C(CCCCC1SCC2NC(=O)NC21)NCCOCCOCCOCCOCCC(=O)NCCCOc1ccc(C(=O)c2ccc(NCCCOCCOCCOCCCNC(=O)CCN3C(=O)C=CC3=O)cc2)cc1]

2,5-dioxopyrrolidin-1-yl 3-(2,5-dioxo-2,5-dihydro-1H-pyrrol-1-yl)propanoate (0.65 g, 2.43 mmol) was added to a solution of crude N-(3-(4-(4-((3-(2-(2-(3-aminopropoxy)ethoxy)ethoxy)propyl)amino)-benzoyl)phenoxy)propyl)-1-(5-(2-oxohexahydro-1H-thieno[3,4-d]imidazol-4-yl)pentanamido)-3,6,9,12-tetraoxapentadecan-15-amide (2 g, 2.11 mmol) in DCM (20 mL) and the reaction mixture was stirred for 2 hs at room temperature. Upon completion, reaction was then concentrated under reduced pressure, and purified by silica gel chromatography (DCM to DCM:MeOH, gradient) to yield 1.70 g (1.55 mmol, 73%) N-(3-(4-(4-((17-(2,5-dioxo-2,5-dihydro-1H-pyrrol-1-yl)-15-oxo-4,7,10-trioxa-14-azaheptadecyl)-amino)benzoyl)phenoxy)propyl)-1-(5-(2-oxohexahydro-1H-thieno[3,4-d]imidazol-4-yl)pentanamido)-3,6,9,12-tetraoxapentadecan-15-amide as yellow oil.

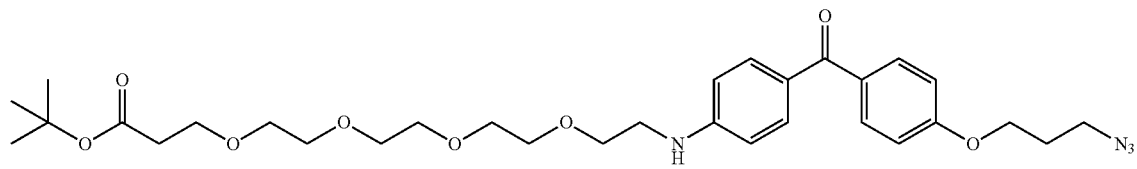 [SMILES: CC(C)(C)OC(=O)CCOCCOCCOCCOCCNc1ccc(C(=O)c2ccc(OCCCN=[N+]=[N-])cc2)cc1]

2-Acetylcyclohexanone (214 mg, 1.53 mmol), cesium carbonate (2.0 g, 5.09 mmol), amino-dPEG4-t-butyl ester (Quanta BioDesign Ltd) (1.72 g, 5.34 mmol), and copper(I) iodide (145 mg, 0.76 mmol) and (4-(3-azidopropoxy)phenyl)(4-iodophenyl)methanone (2.0 g, 5.09 mmol) were combined in anhydrous DMF (14 ml). The flask was vacuumed and backfilled with argon three times, sealed and stirred r.t. for 3-4 hs. Upon completion, reaction was concentrated and purified silica gel chromatography (EtOAc:Hex gradient) to yield 2.53 g (82.0% yield) of tert-butyl 1-((4-(4-(3-azidopropoxy)benzoyl)phenyl)amino)-3,6,9,12-tetraoxapentadecan-15-oate as yellow oil.

;1

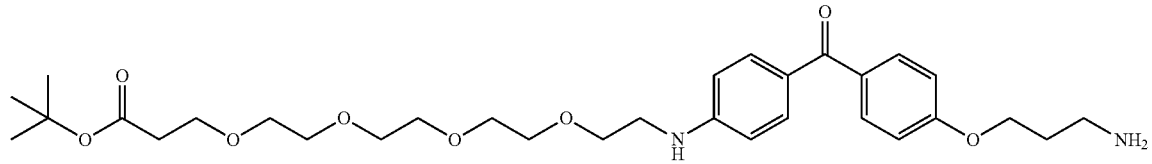 [SMILES: CC(C)(C)OC(=O)CCOCCOCCOCCOCCNc1ccc(C(=O)c2ccc(OCCCN)cc2)cc1]

Triphenylphosphine (2.62 g, 10.0 mmol) was added to a solution of tert-butyl 1-((4-(4-(3-azidopropoxy)benzoyl)phenyl)amino)-3,6,9,12-tetraoxapentadecan-15-oate (5.0 g 8.32 mmol) in Ether:THF (1:1, 50 mL) at 0° C. followed by of water (500 mg, 27.8 mmol). The reaction was stirred at r.t. overnight. Upon completion, the reaction was concentrated and purified by silica gel chromatography (EtOAc to EtOAc:MeOH gradient with 1% TEA) to provide 3.24 g (5.63 mmo 68.7% yield) of tert-butyl 1-((4-(4-(3-aminopropoxy)benzoyl)phenyl)amino)-3,6,9,12-tetraoxapentadecan-15-oate as yellow oil.

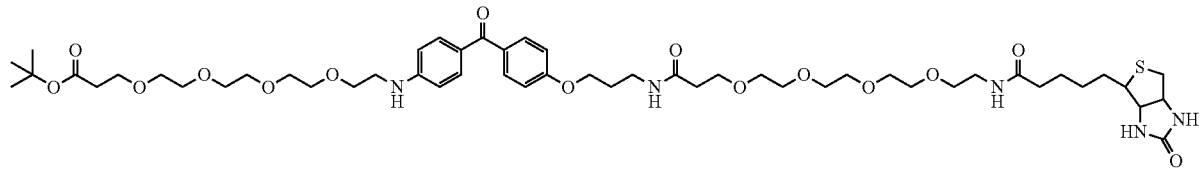 [SMILES: CC(C)(C)OC(=O)CCOCCOCCOCCOCCNc1ccc(C(=O)c2ccc(OCCCNC(=O)CCOCCOCCOCCOCCNC(=O)CCCCC3SCC4NC(=O)NC43)cc2)cc1]

NHS-dPEG4-biotin (Quanta BioDesign Ltd, 3.07 g, 5.97 mmol) was added to a solution of tert-butyl 1-((4-(4-(3-azidopropoxy)benzoyl)phenyl)amino)-3,6,9,12-tetraoxapentadecan-15-oate (3.21 g, 5.62 mmol) in anhydrous DCM (30 ml) and the reaction mixture was stirred at r.t. for 3 hs. Upon completion, reaction was concentrated under reduced pressure and purified by silica gel chromatography (DCM to DCM:MeOH, gradient) to yield 5.3 g (92.0% yield) of tert-butyl 1-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)-3,6,9,12-tetraoxapentadecan-15-oate as slightly yellow oil.

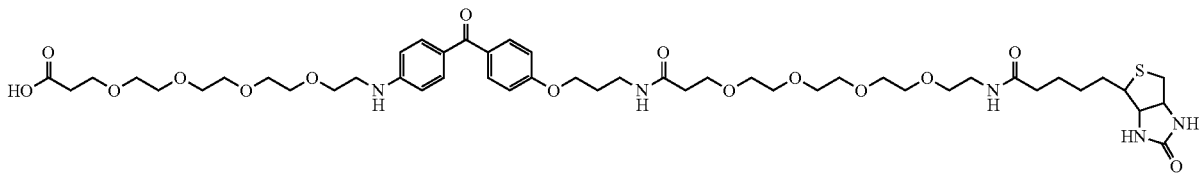 [SMILES: O=C(O)CCOCCOCCOCCOCCNc1ccc(C(=O)c2ccc(OCCCNC(=O)CCOCCOCCOCCOCCNC(=O)CCCCC3SCC4NC(=O)NC43)cc2)cc1]

tert-butyl 1-((4-(4-((5,21-dioxo-25-(2-oxohexahydro-1H-thieno[3,4-d]imidazo-4-yl)-8,11,14,17-tetraoxa-4,20-diazapentacosyl)oxy)benzoyl)-phenyl)amino)-3,6,9,12-tetraoxapentadecan-15-oate (5.34 gr, 5.16 mmol) was dissolved in a solution of DCM:TFA (2:1, 36 ml) and the reaction mixture was stirred for ca. 1 h at r.t. Upon completion, reaction was then concentrated under reduced pressure, co-evaporated with toluene, and dried on pump for 5 hs to yield 3.73 g (73.9% yield) of crude 1-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)-3,6,9,12-tetraoxapentadecan-15-oic acid as yellow oil.

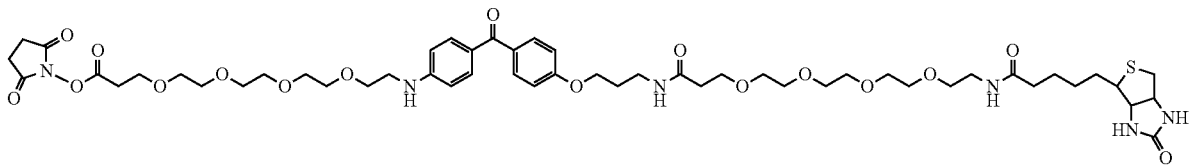 [SMILES: O=C(CCCCC1SCC2NC(=O)NC21)NCCOCCOCCOCCOCCC(=O)NCCCOc1ccc(C(=O)c2ccc(NCCOCCOCCOCCOCCC(=O)ON3C(=O)CCC3=O)cc2)cc1]

To a solution of crude 1-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)-3,6,9,12-tetraoxapentadecan-15-oic acid (1.85 g, 1.89 mmol) in anhydrous DCM (43.0 ml) was added N-hydroxysuccinimide (239 mg, 2.08 mmol) followed by EDC (471 mg, 2.46 mmol). The reaction was stirred at r.t. for 4 hs. Upon completion, reaction was concentrated under reduced pressure and purified by silica gel chromatography (DCM to DCM:iPrOH, gradient) to provide 2,5-dioxopyrrolidin-1-yl 1-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)-3,6,9,12-tetraoxapentadecan-15-oate as slightly yellow oil.

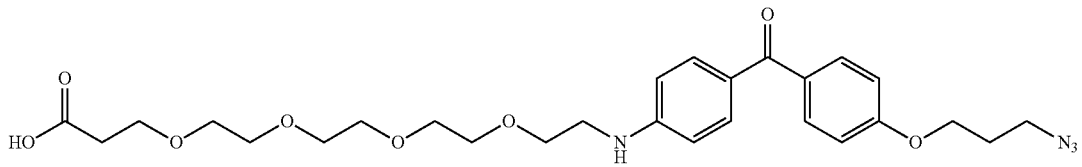 [SMILES: [N-]=[N+]=NCCCOc1ccc(C(=O)c2ccc(NCCOCCOCCOCCOCCC(=O)O)cc2)cc1]

tert-butyl-(2-(2-(2-(2-((4-(4-(3-azidopropoxy)benzoyl)phenyl)-amino)ethoxy)ethoxy)ethoxy)ethyl)-carbamate (1.75 g, 2.91 mmol) was dissolved in a solution of DCM:TFA (2:1, 12 ml) and left to stir for ca. 1 h. Upon completion, reaction was then concentrated under reduced pressure, co-evaporated with toluene, and left on oil pump for 5 hs to yield 1.52 g (97.0% yield) of (2-(2-(2-(2-((4-(4-(3-azidopropoxy)benzoyl)phenyl)-amino)ethoxy)ethoxy)ethoxy)ethyl)carboxylic acid as colorless oil.

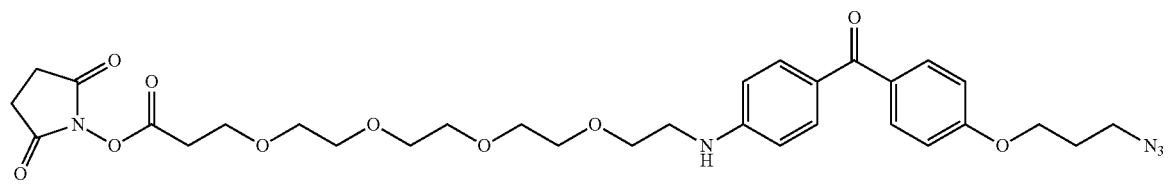 [SMILES: [N-]=[N+]=NCCCOc1ccc(C(=O)c2ccc(NCCOCCOCCOCCOCCC(=O)ON3C(=O)CCC3=O)cc2)cc1]

N-hydroxysuccinimide (358 mg, 3.11 mmol) was added to a solution of (2-(2-(2-(2-((4-(4-(3-azidopropoxy)benzoyl)phenyl)-amino)ethoxy)ethoxy)ethoxy)ethyl)carboxylic acid (1.54 g, 2.83 mmol) in anhydrous DCM (20 ml) was added followed by EDC (651 mg, 3.39 mmol). The reaction was stirred at r.t. for 2-3 hs. Upon completion, reaction was concentrated under reduced pressure and purified by silica gel chromatography (DCM to DCM:iPrOH gradient) to provide 1.68 g (93.0% yield) of 2,5-dioxopyrrolidin-1-yl 1-((4-(4-(3-azidopropoxy)benzoyl)phenyl)amino)-3,6,9,12-tetraoxapentadecan-15-oate as slightly yellow oil.

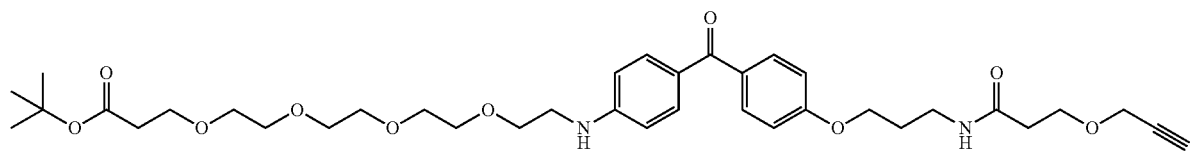 [SMILES: C#CCOCCC(=O)NCCCOc1ccc(C(=O)c2ccc(NCCOCCOCCOCCOCCC(=O)OC(C)(C)C)cc2)cc1]

EDC (0.77 g, 4.00 mmol) was added to a solution of tert-butyl 1-((4-(4-(3-aminopropoxy)benzoyl)phenyl)amino)-3,6,9,12-tetraoxapentadecan-15-oate (2.00 g, 3.48 mmol), 3-(prop-2-yn-1-yloxy)propanoic acid (0.45 g, 3.48 mmol) and N-hydroxysuccinimide (0.06 g, 0.52 mmol) in DCM (12 mL) at r.t. and the reaction mixture was stirred for 4 hs at room temperature. Upon completion, reaction was concentrated under reduced pressure and purified by silica gel chromatography (EtOAc to EtOAc:MeOH, gradient) to provide 2.12 g (3.10 mmol, 89% yield) of tert-butyl 1-((4-(4-(3-(3-(prop-2-yn-1-yloxy)propanamido)propoxy)benzoyl)phenyl)amino)-3,6,9,12-tetraoxapentadecan-15-oate as slightly yellow oil.

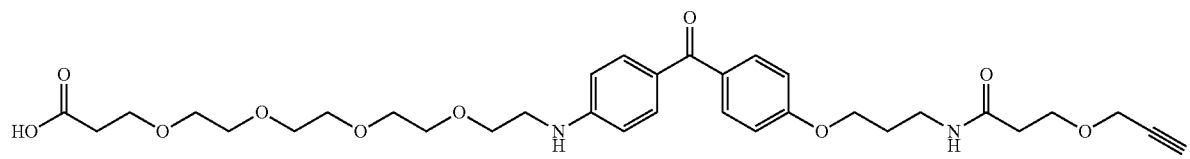 [SMILES: C#CCOCCC(=O)NCCCOc1ccc(C(=O)c2ccc(NCCOCCOCCOCCOCCC(=O)O)cc2)cc1]

tert-butyl 1-((4-(4-(3-(3-(prop-2-yn-1-yloxy)propanamido)propoxy)benzoyl)phenyl)amino)-3,6,9,12-tetraoxapentadecan-15-oate (2.12 g, 3.10 mmol) was dissolved in (15 ml) and the reaction mixture was stirred at 45 C for ca. 1 h. Upon completion, reaction was concentrated under reduced pressure, co-evaporated with toluene, and purified by silica gel chromatography (EtOActoEtOAc:MeOH gradient) to provide 1.25 g (1.98 mmol, 65% yield) of 1-((4-(4-(3-(3-(prop-2-yn-1-yloxy)propanamido)propoxy)-benzoyl)phenyl)amino)-3,6,9,12-tetraoxapentadecan-15-oic acid as slightly yellow oil.

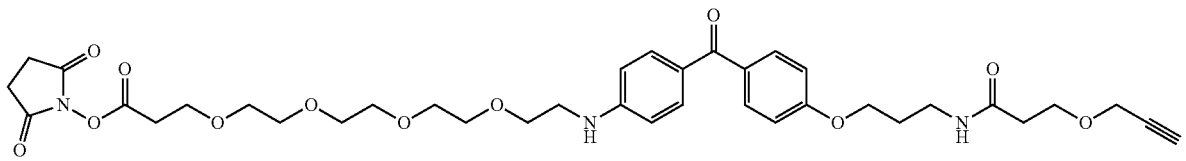 [SMILES: C#CCOCCC(=O)NCCCOc1ccc(C(=O)c2ccc(NCCOCCOCCOCCOCCC(=O)ON3C(=O)CCC3=O)cc2)cc1]

N-hydroxysuccinimide (252 mg, 2.30 mmol) was added to a solution of 1-((4-(4-(3-(3-(prop-2-yn-1-yloxy)propanamido)propoxy)benzoyl)phenyl)amino)-3,6,9,12-tetraoxapentadecan-15-oic acid (1.25 g, 1.98 mmol) in anhydrous DCM (10 ml) was added followed by EDC (505 mg, 2.64 mmol). The reaction was stirred at r.t. for 2-3 hs. Upon completion, reaction was concentrated under reduced pressure and purified by silica gel chromatography (DCM to DCM:iPrOH gradient) to provide 1.16 g (1.63 mmol, 80% yield) of 2,5-dioxopyrrolidin-1-yl 1-((4-(4-(3-(3-(prop-2-yn-1-yloxy)propanamido)propoxy)benzoyl)phenyl)amino)-3,6,9,12-tetraoxapentadecan-15-oate as slightly yellow oil.

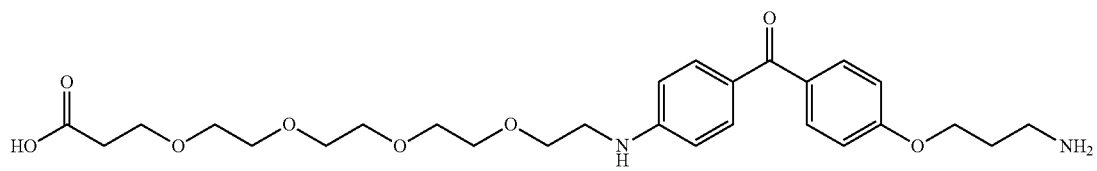 [SMILES: NCCCOc1ccc(C(=O)c2ccc(NCCOCCOCCOCCOCCC(=O)O)cc2)cc1]

tert-butyl 1-((4-(4-(3-aminopropoxy)benzoyl)phenyl)amino)-3,6,9,12-tetraoxapentadecan-15-oate (3.24 g, 5.63 mmol) was dissolved in a solution of DCM:TFA (2:1, 20 ml) and stirred ca. 1 h. Upon completion, reaction was then concentrated under reduced pressure, co-evaporated with toluene, and dried on oil pump for 5 hs to yield 3.20 g of crude 1-((4-(4-(3-aminopropoxy)benzoyl)phenyl)amino)-3,6,9,12-tetraoxapentadecan-15-oic acid as yellow oil. The crude product was used without any further purification.

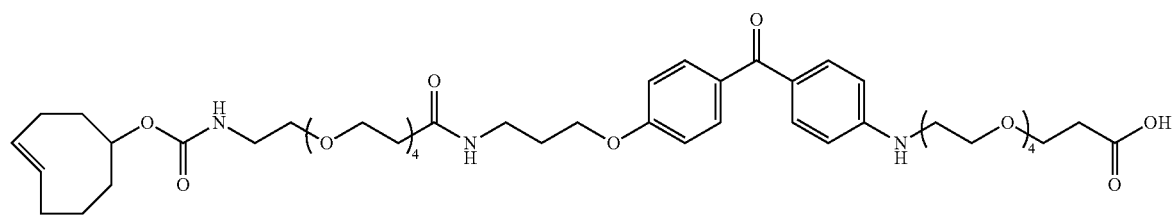

A solution of TCO-PEG4-NHS ester (0.5 g, 0.971 mmol, Click Chemistry Tools, Scottsdale, Ariz.) in DCM (5 mL) was added to a solution of crude 1-((4-(4-(3-aminopropoxy)benzoyl)phenyl)amino)-3,6,9,12-tetraoxapentadecan-15-oic acid (0.65 g, 1.25 mmol) and Et₃N (2 mL, 19.80 mmol) and the reaction mixture was stirred for ca. 4 hs at r.t. Upon completion, reaction was concentrated under reduced pressure, co-evaporated with toluene, and purified by silica gel chromatography (EtOActoEtOAc:MeOH gradient) to provide 0.72 g (0.784 mmol, 81% yield) of TCO-PEG4-benzophenone-PEG4-acid.

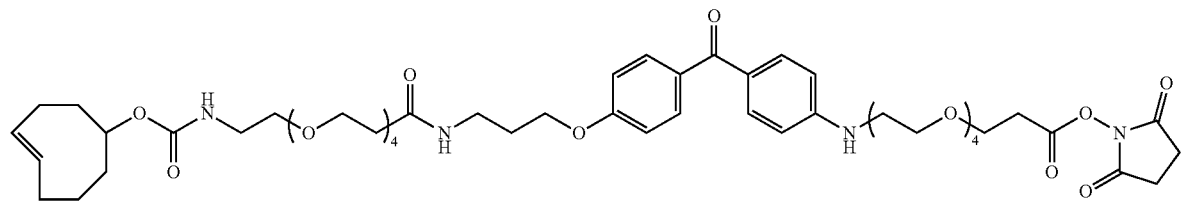

N-hydroxysuccinimide (126 mg, 1.15 mmol) was added to a solution of TCO-PEG4-benzophenone-PEG4-acid (0.72 g, 0.784 mmol) in anhydrous DCM (5 ml) was added followed by EDC (250 mg, 1.32 mmol). The reaction was stirred at r.t. for 2-3 hs. Upon completion, reaction was concentrated under reduced pressure and purified by silica gel chromatography (DCM to DCM:iPrOH gradient) to provide 0.41 g (0.407 mmol, 52% yield) of TCO-PEG4-benzophenone-PEG4-NHS ester.

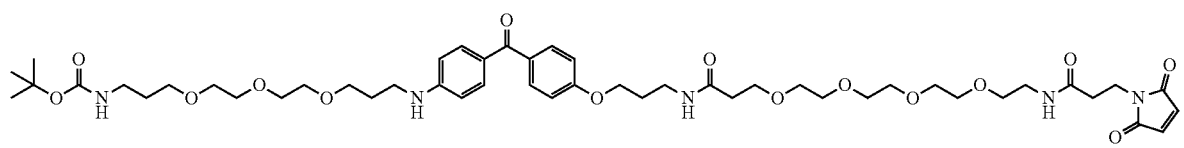 [SMILES: CC(C)(C)OC(=O)NCCCOCCOCCOCCCNc1ccc(C(=O)c2ccc(OCCCNC(=O)CCOCCOCCOCCOCCNC(=O)CCN3C(=O)C=CC3=O)cc2)cc1]

Maleimide-dPEG4-NHS ester (5.00 g, 9.75 mmol, Quanta BioDesign Ltd,) was added to a solution of tert-butyl-(3-(2-(3-(3-((4-(4-(3-aminopropoxy)benzoyl)phenyl)amino)propoxy)propoxy)ethoxy)propyl)carbamate (5.00 g, 8.51 mmol) in anhydrous DCM (30 ml) and the reaction mixture was stirred at r.t. for 3 hs. Upon completion, reaction was concentrated under reduced pressure and purified by silica gel chromatography (DCM to DCM:MeOH, gradient) to yield 6.31 g (6.50 mmol, 76% yield) of tert-butyl (3-(2-(2-(3-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)propoxy)ethoxy)ethoxy)propyl)carbamate as yellow oil.

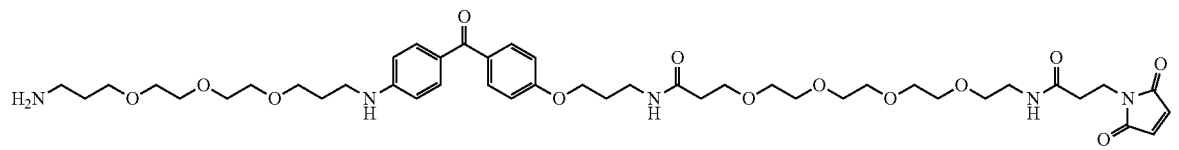 [SMILES: NCCCOCCOCCOCCCNc1ccc(C(=O)c2ccc(OCCCNC(=O)CCOCCOCCOCCOCCNC(=O)CCN3C(=O)C=CC3=O)cc2)cc1]

tert-butyl (3-(2-(2-(3-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)propoxy)ethoxy)ethoxy)propyl)carbamate (6.31 g, 6.50 mmol) was dissolved in a solution of DCM:TFA (2:1, 60 ml) and stirred ca. 1 h. Upon completion, reaction was then concentrated under reduced pressure, co-evaporated with toluene, and dried on oil pump for 2 hs to yield 6.15 g of crude N-(3-(4-(4-((3-(2-(2-(3-aminopropoxy)ethoxy)ethoxy)propyl)-amino)benzoyl)phenoxy)propyl)-1-(3-(2,5-dioxo-2,5-dihydro-1H-pyrrol-1-yl)propanamido)-3,6,9,12-tetraoxapentadecan-15-amide as yellow oil. The crude product was used without any further purification.

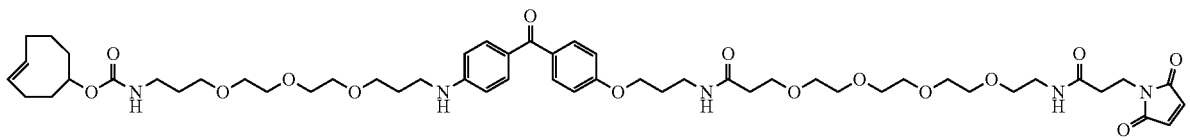 [SMILES: O=C(CCOCCOCCOCCOCCNC(=O)CCN1C(=O)C=CC1=O)NCCCOc1ccc(C(=O)c2ccc(NCCCOCCOCCOCCCNC(=O)OC3CC/C=C/CCC3)cc2)cc1]

A solution of TCO-NHS ester (0.5 g, 1.87 mmol, Click Chemistry Tools, Scottsdale, Ariz.) in DCM (10 mL) was added to a solution of crude N-(3-(4-(4-((3-(2-(2-(3-aminopropoxy)ethoxy)ethoxy)propyl)-amino)benzoyl)phenoxy)propyl)-1-(3-(2,5-dioxo-2,5-dihydro-1H-pyrrol-1-yl)propanamido)-3,6,9,12-tetraoxapentadecan-15-amide (2.0 g, 2.29 mmol) and Et₃N (2 mL) in DCM (30 mL) and the reaction mixture was stirred for ca. 2 hs at r.t. Upon completion, reaction was concentrated under reduced pressure, and purified by silica gel chromatography (EtOActoEtOAc:MeOH gradient) to provide 1.35 g (1.31 mmol, 70% yield) of TCO-PEG4-benzophenone-PEG4-Maleimide as slightly yellow oil.

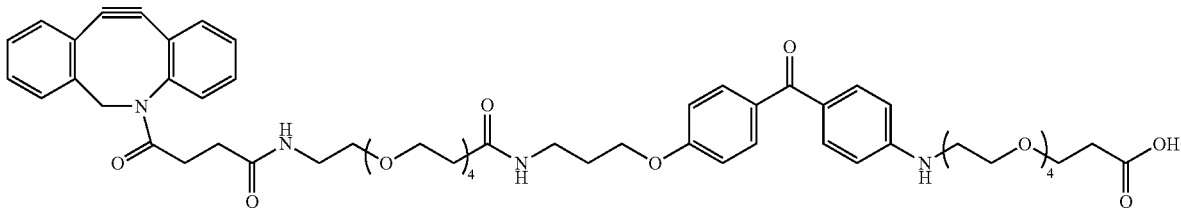

A solution of DBCO-PEG4-NHS ester (0.65 g, 1.00 mmol, Click Chemistry Tools, Scottsdale, Ariz.) in DCM (5 mL) was added to a solution of crude 1-((4-(4-(3-aminopropoxy)benzoyl)phenyl)amino)-3,6,9,12-tetraoxapentadecan-15-oic acid (0.65 g, 1.25 mmol) and Et₃N (2 mL, 19.80 mmol) and the reaction mixture was stirred for ca. 4 hs at r.t. Upon completion, reaction was concentrated under reduced pressure, and purified by silica gel chromatography (EtOActoEtOAc:MeOH gradient) to provide 0.80 g (0.76 mmol, 76% yield) of DBCO-PEG4-benzophenone-PEG4-acid as slightly yellow oil.

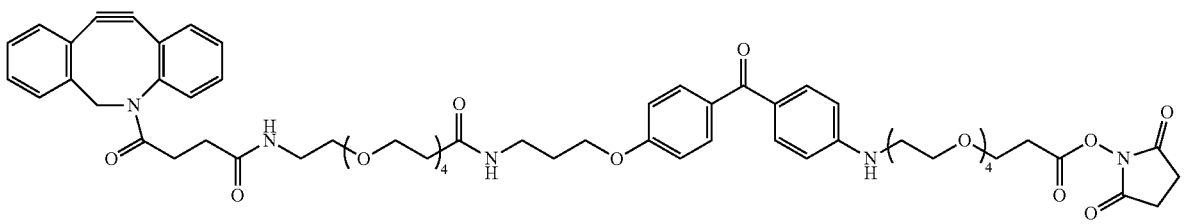

N-hydroxysuccinimide (126 mg, 1.15 mmol) was added to a solution of DBCO-PEG4-benzophenone-PEG4-acid (0.80 g, 0.76 mmol) in anhydrous DCM (5 ml) was added followed by EDC (250 mg, 1.32 mmol). The reaction was stirred at r.t. for 2-3 hs. Upon completion, reaction was concentrated under reduced pressure and purified by silica gel chromatography (DCM to DCM:iPrOH gradient) to provide 0.55 g (0.47 mmol, 62% yield) of DBCO-PEG4-benzophenone-PEG4-NHS ester.

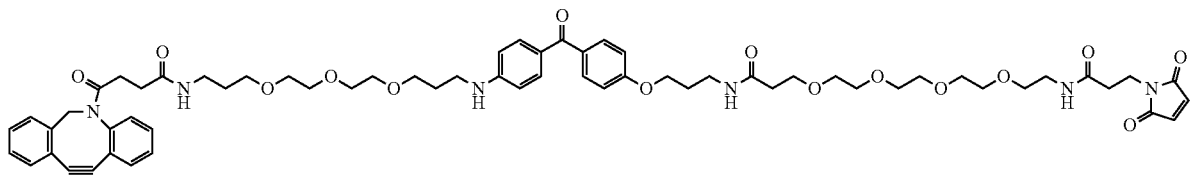 [SMILES: O=C(CCOCCOCCOCCOCCNC(=O)CCN1C(=O)C=CC1=O)NCCCOc1ccc(C(=O)c2ccc(NCCCOCCOCCOCCCNC(=O)CCC(=O)N3Cc4ccccc4C#Cc4ccccc43)cc2)cc1]

A solution of DBCO-NHS ester (1.0 g, 2.49 mmol, Click Chemistry Tools, Scottsdale, Ariz.) in DCM (10 mL) was added to a solution of crude N-(3-(4-(4-((3-(2-(2-(3-aminopropoxy)ethoxy)ethoxy)propyl)amino)benzoyl)phenoxy) propyl)-1-(3-(2,5-dioxo-2,5-dihydro-1H-pyrrol-1-yl)propanamido)-3,6,9,12-tetraoxapentadecan-15-amide (2.5 g, 2.86 mmol) and Et$_3$N (2.5 mL) in DCM (40 mL) and the reaction mixture was stirred for ca. 2 hs at r.t. Upon completion, reaction was concentrated under reduced pressure, and purified by silica gel chromatography (EtOActoEtOAc: MeOH gradient) to provide 1.63 g (1.41 mmol, 56% yield) of DBCO-PEG4-benzophenone-PEG4-Maleimide as slightly yellow oil.

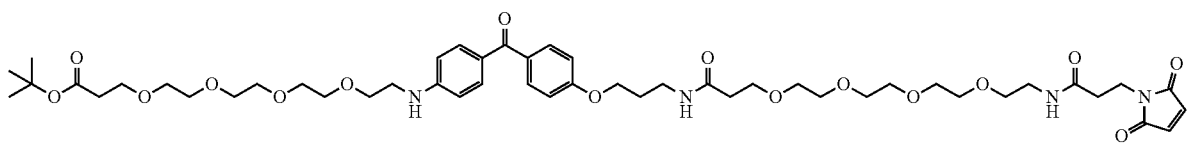 [SMILES: CC(C)(C)OC(=O)CCOCCOCCOCCOCCNc1ccc(C(=O)c2ccc(OCCCNC(=O)CCOCCOCCOCCOCCNC(=O)CCN3C(=O)C=CC3=O)cc2)cc1]

Maleimide-dPEG4-NHS ester (5.00 g, 9.75 mmol, Quanta BioDesign Ltd,) was added to a solution of tert-butyl 1-((4-(4-(3-azidopropoxy)benzoyl)phenyl)amino)-3,6,9,12-tetraoxapentadecan-15-oate (5.00 g, 8.77 mmol) in anhydrous DCM (30 ml) and the reaction mixture was stirred at r.t. for 3 hs. Upon completion, reaction was concentrated under reduced pressure and purified by silica gel chromatography (DCM to DCM:MeOH, gradient) to yield 7.36 g (7.85 mmol, 90.0% yield) of tert-butyl 1-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)-3,6,9,12-tetraoxapentadecan-15-oate as yellow oil.

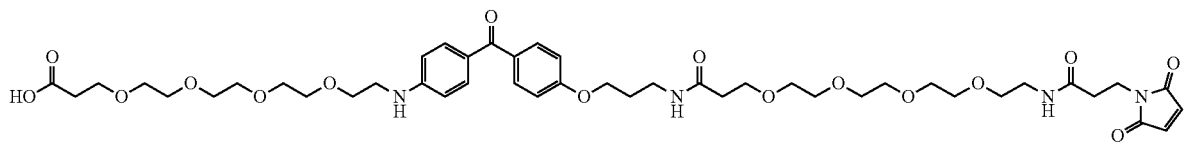 [SMILES: O=C(O)CCOCCOCCOCCOCCNc1ccc(C(=O)c2ccc(OCCCNC(=O)CCOCCOCCOCCOCCNC(=O)CCN3C(=O)C=CC3=O)cc2)cc1]

tert-butyl 1-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)-3,6,9,12-tetraoxapentadecan-15-oate (7.36 g, 7.85 mmol) was dissolved in a solution of DCM:TFA (2:1, 50 ml) and left to stir for ca. 1 h. Upon completion, reaction was then concentrated under reduced pressure, co-evaporated with toluene, and dried on oil pump overnight to yield 8.35 g of crude 1-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)-3,6,9,12-tetraoxapentadecan-15-oic acid as yellow oil.

using the molar extinction coefficients for both protein and spectrophotometrically quantifiable biotin as found in Table 1.

TABLE 1

| Component | Molar extinction coefficient at 280 mm ($M^{-1}cm^{-1}$) | Molar extinction coefficient at 350 nm ($M^{-1}cm^{-1}$) |
| --- | --- | --- |
| Traceable Biotin Reagent (Compound 1) | 8,715 | 19,747 |

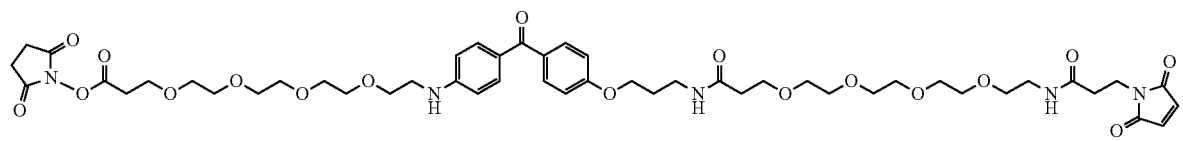 [SMILES: O=C(CCOCCOCCOCCOCCNC(=O)CCN1C(=O)C=CC1=O)NCCCOc1ccc(C(=O)c2ccc(NCCOCCOCCOCCOCCC(=O)ON3C(=O)CCC3=O)cc2)cc1]

N-hydroxysuccinimide (438 mg, 4.00 mmol) was added to a solution of crude 1-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)-3,6,9,12-tetraoxapentadecan-15-oic acid (3.00 g) in anhydrous DCM (20 ml) was added followed by EDC (946 mg, 5.00 mmol). The reaction was stirred at r.t. for 2-3 hs. Upon completion, reaction was concentrated under reduced pressure and purified by silica gel chromatography (DCM to DCM:iPrOH gradient) to provide 2.15 g (2.12 mmol) of 2,5-dioxopyrrolidin-1-yl 1-((4-(4-((1-(2,5-dioxo-2,5-dihydro-1H-pyrrol-1-yl)-3,19-dioxo-7,10,13,16-tetraoxa-4,20-diazatricosan-23-yl)oxy)benzoyl)phenyl)amino)-3,6,9,12-tetraoxapentadecan-15-oate as slightly yellow oil.

Protein Conjugates Using Spectrophotometrically Quantifiable Biotin NHS Reagents A series of biotin labeled bovine serum albumin and goat IgG conjugates were prepared by standard methods using 2,5-dioxopyrrolidin-1-yl 1-((4-(4-((5,21-dioxo-25-(2-oxohexahydro-1H-thieno[3,4-d]imidazol-4-yl)-8,11,14,17-tetraoxa-4,20-diazapentacosyl)oxy)benzoyl)phenyl)amino)-3,6,9,12-tetraoxapentadecan-15-oate A stock solution of bovine serum albumin (4.7 mg/mL) is prepared in 100 mM sodium phosphate, 150 mM sodium chloride, pH 7.5. This BSA stock (4.7 mg/mL) is used to prepare a series of nine BSA samples, three at 1 mg/mL, three at 2 mg/mL, and three 4 mg/mL by dilution into the same buffer. Similarly, a stock solution of Goat IgG (5.1 mg/mL) is prepared in 100 mM sodium phosphate, 150 mM sodium chloride, pH 7.5. The Goat IgG stock (5.1 mg/mL) is used to prepare a series of nine GIgG samples, three at 1 mg/mL, three at 2 mg/mL, and three at 4 mg/mL concentrations by dilution into the same buffer. 2,5-dioxopyrrolidin-1-yl 1-((4-(4-((5,21-dioxo-25-(2-oxohexahydro-1H-thieno[3,4-d]imidazol-4-yl)-11,14,17-tetraoxa-4,20-diazapentacosyl)oxy)benzoyl)phenyl)amino)-3,6,9,12-tetraoxapentadecan-15-oate is dissolved in DMSO at various concentrations (6.4 to 40 mg/mL) and appropriate aliquots added to bovine serum albumin and goat IgG samples to achieve molar ratios (5, 10, or 20 equivalents). All reaction mixtures are allowed to incubate for 1 hour at room temperature followed by removal of excess, biotin labeling reagent using size exclusion spin columns equilibrated in 100 mM sodium phosphate, 150 mM sodium chloride, pH 7.5. After removal of excess reagent, the degree of substitution (DOS) is determined from the absorbance maximum of each conjugate at 280 nm and 350 nm TABLE 1-continued

| Component | Molar extinction coefficient at 280 mm ($M^{-1}cm^{-1}$) | Molar extinction coefficient at 350 nm ($M^{-1}cm^{-1}$) |
| --- | --- | --- |
| Bovine Serum Albumin | 44,309 | N/A |
| Goat IgG | 204,000 | N/A |

*extinction coefficient for biotin reagent were determined for free carboxylic acid in 100 mM sodium phosphate, 150 mM sodium chloride, pH 7.5. Coefficients for BSA and Goat IgG were determined from published E1% @ 280 nm, 6.7 and 13.6, respectively.

Protein Conjugates Using Spectrophotometrically Quantifiable Biotin Maleimide Reagents A series of biotin labeled Goat IgG conjugates were prepared by standard methods using a thiol-reactive maleimide ester of a spectrophotometrically quantifiable biotin labeling reagent, N-(3-(4-(4-((17-(2,5-dioxo-2,5-dihydro-1H-pyrrol-1-yl)-15-oxo-4,7,10-trioxa-14-azaheptadecyl)amino)benzoyl)phenoxy)propyl)-1-(5-(2-oxohexahydro-1H-thieno[3,4-d]imidazol-4-yl)pentanamido)-3,6,9,12-tetraoxapentadecan-15-amide A stock solution of Goat IgG (4.77 mg/mL) is prepared in 100 mM sodium phosphate, 150 mM sodium chloride, pH 6.5. This stock solution is used to prepare triplicate samples (0.5 mL each at 0.5 mg/mL) and (0.5 mL each at 2 mg/mL). Five L of 500 mM EDTA pH 8.0 is then added to each of these six samples, immediately followed by addition of freshly prepared 105 mM TCEP-HCl in water (25 uL) to achieve a final TCEP concentration of 5 mM. TCEP reduction reactions are incubated for 30 minutes to fully reduce disulfide bonds in IgG to free thiolate ions. Excess TCEP reducing reagent is then removed by size exclusion spin columns equilibrated in 100 mM sodium phosphate, 150 mM sodium chloride containing 1 mM EDTA, pH 6.5. N-(3-(4-(4-((17-(2,5-dioxo-2,5-dihydro-1H-pyrrol-1-yl)-15-oxo-4,7,10-trioxa-14-azaheptadecyl)amino)benzoyl)phenoxy)propyl)-1-(5-(2-oxohexahydro-1H-thieno[3,4-d]imidazol-4-yl)pentanamido)-3,6,9,12-tetraoxapentadecan-15-amide is dissolved in DMSO (4.67 mg/mL) and appropriate aliquots added to reduced goat IgG at 0.5 mg/mL (triplicates) to achieve a 20-fold molar excess reagent over IgG. Similarly, traceable biotin labeling reagent is dissolved (20.67 mg/mL) and appropriate aliquots added to goat IgG at 2.0 mg/mL to achieve a 20-fold molar excess over IgG. The maleimide labeling reaction mixtures are allowed to incubate for 1 hour at room temperature followed by removal of excess biotin reagent using size exclusion spin columns equilibrated in 100 mM sodium phosphate, 150 mM sodium chloride, pH 7.5 (no EDTA). The degree of substitution (DOS) is determined from the absorbance maximum of each conjugate at 280 nm and 350 nm using the molar extinction coefficients for Goat IgG and spectrophotometrically quantifiable biotin reagent as found in Table 2.

TABLE 2

| Component | Molar extinction coefficient at 280 nm ($M^{-1}cm^{-1}$) | Molar extinction coefficient at 350 nm ($M^{-1}cm^{-1}$) |
|---|---|---|
| Traceable Biotin Reagent (Compound 2) | 8,715 | 19,747 |
| Goat IgG | 204,000 | N/A |

*extinction coefficient for biotin reagent was determined for free carboxylic acid in 100 mM sodium phophate, 150 mM sodium chloride, pH 7.5. Coefficient for Goat IgG was determined from known E.1% @ 280 nm = 13.6

What is claimed is:

1. A spectrophotometrically quantifiable linker of the following formula:

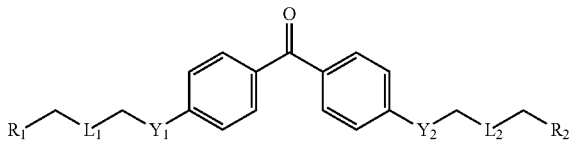

wherein, $R_1$ and $R_2$ are the same or different and are each independently selected from the group consisting of —O—, —OH, —SH, —NH, —$NH_2$, —F, —Cl, —Br, —I, O—Su (N-hydroxysuccinimidyl, sulfo-N-hydroxysuccinimidyl), —O-STP (4-sulfo-2,3,5,6,-tetrafluorophenyl), —O-TFP (2,3,5,6-pentafluorophenyl), —O-benzotriazole, benzotriazole, —CO—$CH_2$—I, —NR-biomolecule wherein the biomolecule is a peptide, protein, antibody, nucleotide, or oligonucleotide, —COO—, —COOH, —CO—NH—$NH_2$, —O-phosphoramidite, —CHO, -maleimide, pyridylsulfide, —O—$NH_2$ (aminoxy), —$N_3$, terminal alkyne, norbornene, tran-cyclooctene, cyclooalkyne, dibenzocyclooctyne, tetrazine, biotin, desthiobiotin, digoxigenin, and hapten;

$L_1$ and $L_2$ are the same or different and are independently selected from the group consisting of a divalent linear —(CH2)$_x$— group, or —(CH2CH2O)$_x$— group, wherein x is 1 to 25, a branched or cyclic alkane group, which is optionally substituted by at least one atom selected from the group consisting of oxygen, substituted nitrogen, and sulfur; and one of $Y_1$ and $Y_2$ is O—, and the other of $Y_1$ and $Y_2$ is NH—, or NR, wherein R is selected from the group consisting of a linear or cyclic —(CH2)$_x$—$CH_3$ group, or -(CH2CH2O)$_x$—$CH_3$ group, wherein x is 1 to 25, a branched or cyclic alkane group, which is optionally substituted by at least one atom selected from the group consisting of oxygen, substituted nitrogen, and sulfur.

2. The spectrophotometrically quantifiable linker according to claim 1, wherein

R is a lower alkyl ($C_1$-$C_{10}$) or PEG.

3. The spectrophotometrically quantifiable linker according to claim 1 of the following formula

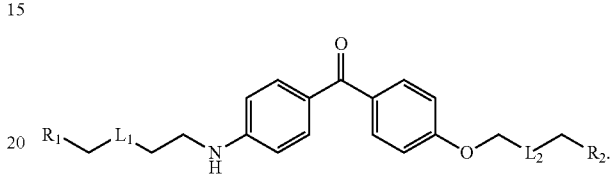

4. The spectrophotometrically quantifiable linker according to claim 1, 2, or 3, wherein at least one of $R_1$ or $R_2$ is hound to a biomolecule.

5. The spectrophotometrically quantifiable linker according to claims 1, 2, or 3, wherein at least one of $R_1$ or $R_2$ is bound to a biomolecule and wherein the biomolecule is part of binding pair selected from the group consisting of receptor ligand binding; biotin avidin binding, peptide S ribonuclease binding, digoxigenin anti-digoxigenin antibody binding, complimentary oligonucleotide pair binding or antibody ligand pairs binding.

6. A process of jointing two molecule comprising of the following steps:
Reacting the spectrophotometrically quantifiable linker according to claims 1, 2, or 3 with a first the biomolecule
Reacting the spectrophotometrically quantifiable linker-biomolecule complex with a second biomolecule.

7. A kit comprising at least one spectrophotometrically quantifiable linker according to claim 1, 2, or 3.

8. The kit according to claim 7 wherein at least one of $R_1$ or $R_2$ of the spectrophotometrically quantifiable linker is biotin, desthiobiotin, digoxigenin.

9. The kit according to claim 7, wherein at least one of $R_1$ or $R_2$ of the spectrophotometrically quantifiable linker is —NR-biomolecule.

10. The kit according to claim 7, wherein at least one of $R_1$ or $R_2$ of the spectrophotometrically quantifiable linker is biotin, desthiobiotin.

11. The spectrophotometrically quantifiable linker which is one of the following compounds,

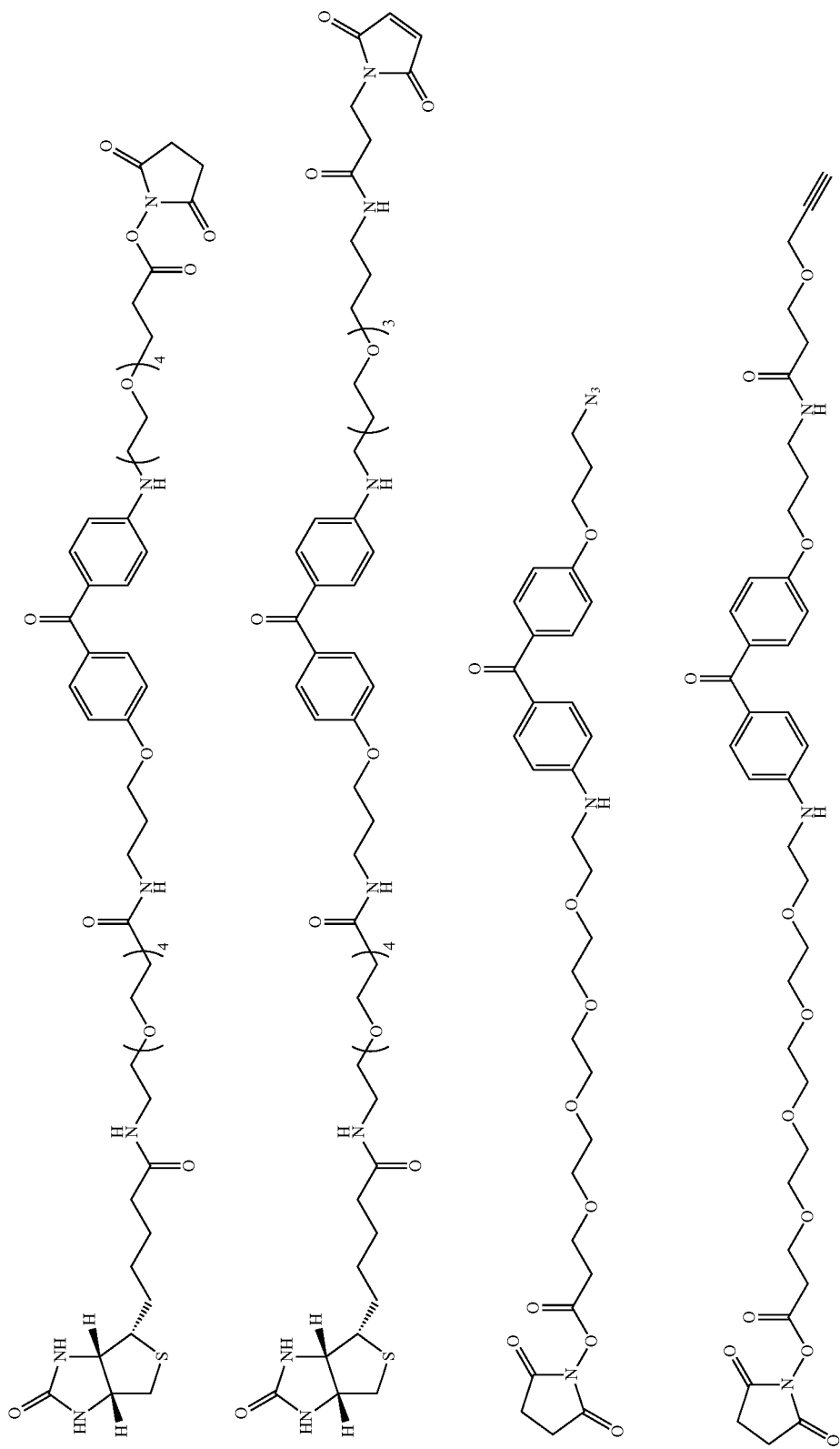

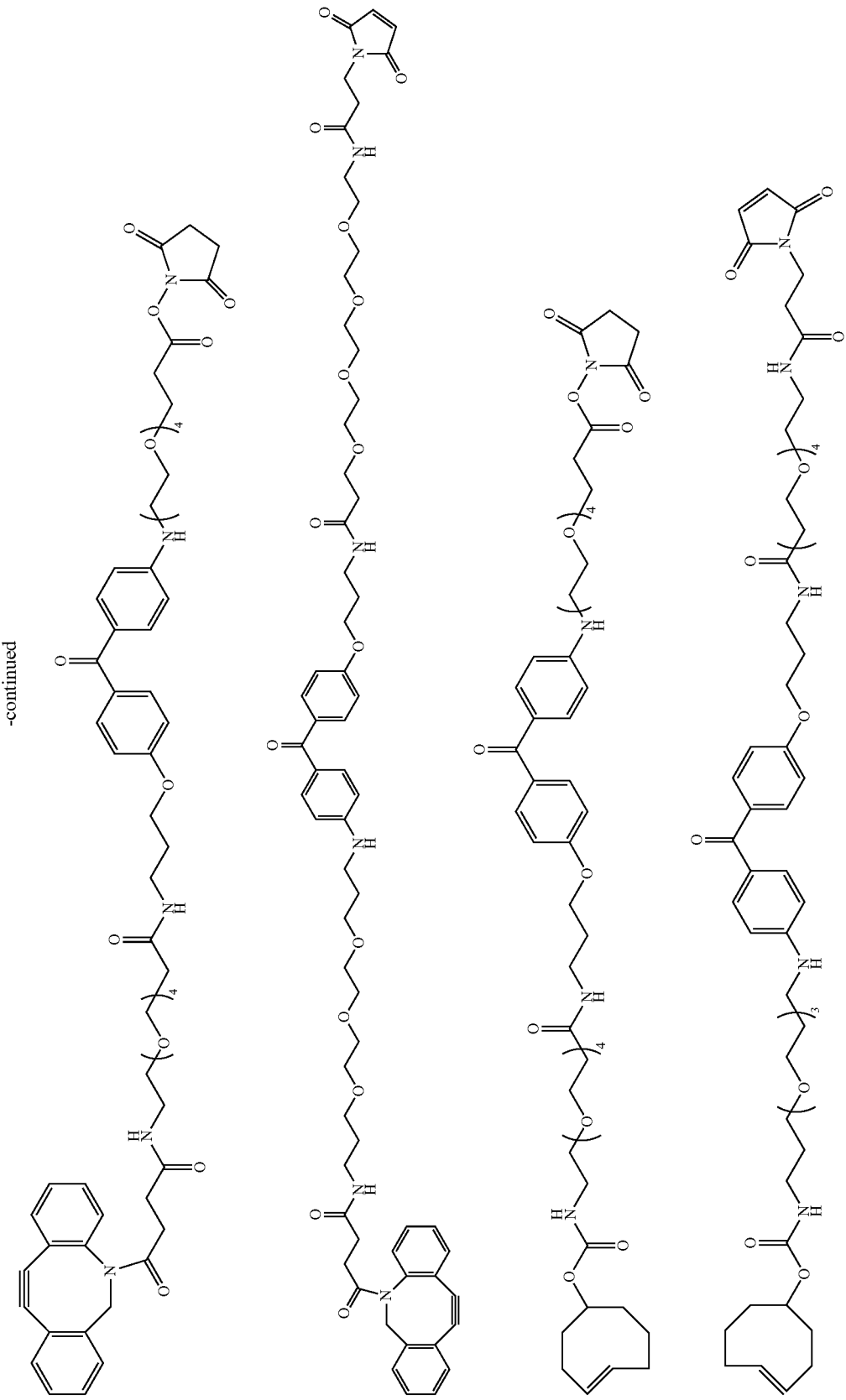

-continued
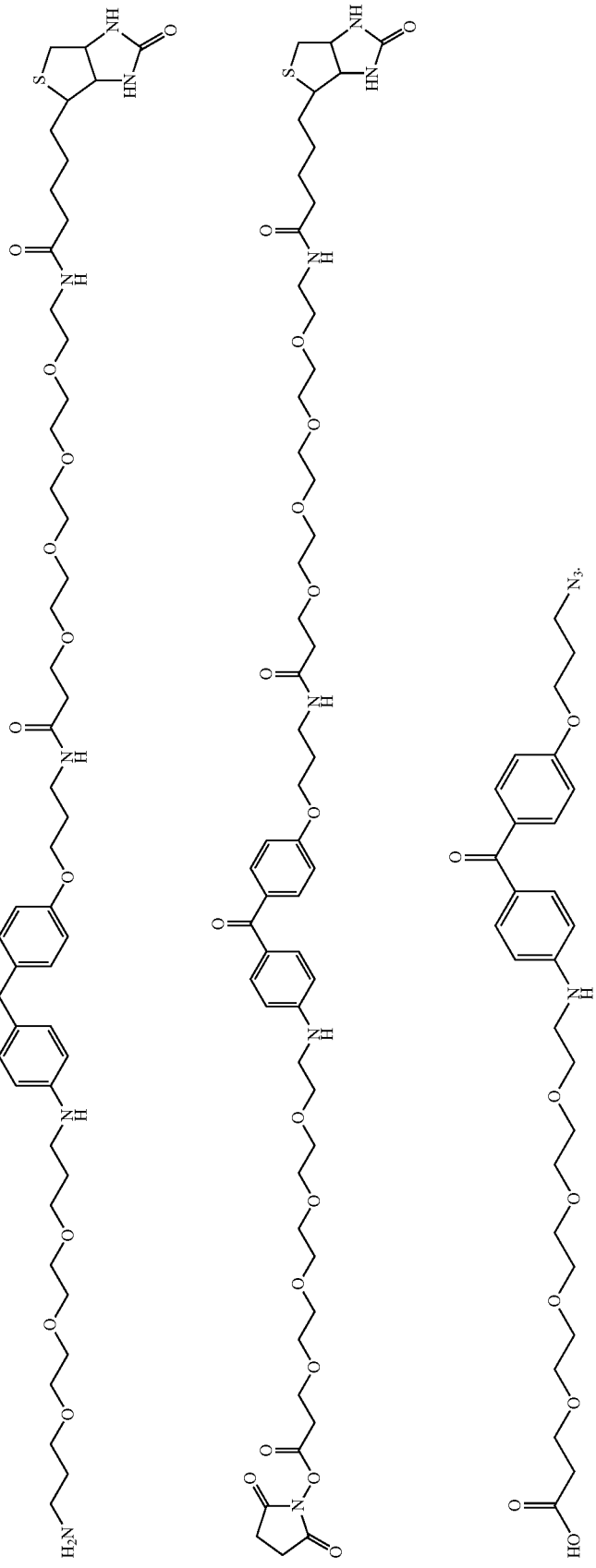

* * * * *